United States Patent
Ginsburg

(10) Patent No.: US 8,506,494 B2
(45) Date of Patent: Aug. 13, 2013

(54) METHOD AND APPARATUS FOR CONTROLLING A PATIENT'S BODY TEMPERATURE BY IN SITU BLOOD TEMPERATURE MODIFICATION

(75) Inventor: Robert Ginsburg, Greenwood Village, CO (US)

(73) Assignee: ZOLL Circulation, Inc., Sunnyvale, CA (US)

( * ) Notice: Subject to any disclaimer, the term of this patent is extended or adjusted under 35 U.S.C. 154(b) by 338 days.

(21) Appl. No.: 11/932,509

(22) Filed: Oct. 31, 2007

(65) Prior Publication Data

US 2008/0114431 A1    May 15, 2008

Related U.S. Application Data

(60) Continuation of application No. 11/044,997, filed on Jan. 26, 2005, which is a continuation of application No. 10/643,321, filed on Aug. 19, 2003, now Pat. No. 6,849,083, which is a continuation of application No. 10/004,579, filed on Dec. 4, 2001, now Pat. No. 6,635,076, which is a continuation of application No. 09/522,135, filed on Mar. 9, 2000, now Pat. No. 6,436,131, which is a continuation of application No. 09/131,081, filed on Aug. 7, 1998, now Pat. No. 6,149,676, which is a division of application No. 08/584,013, filed on Jan. 8, 1996, now Pat. No. 5,837,033, which is a continuation of application No. 08/015,774, filed on Feb. 10, 1993, now abandoned.

(51) Int. Cl.
| | |
|---|---|
| *A61B 5/02* | (2006.01) |
| *A61B 5/00* | (2006.01) |
| *A61F 7/00* | (2006.01) |
| *A61F 7/12* | (2006.01) |

(52) U.S. Cl.
USPC ............. 600/481; 600/549; 607/96; 607/113

(58) Field of Classification Search
USPC ........... 600/481, 483, 504–507, 549; 607/96, 607/113
See application file for complete search history.

(56) References Cited

U.S. PATENT DOCUMENTS

| | | |
|---|---|---|
| 2,308,484 A | 1/1943 | Auzin et al. |
| 3,369,549 A | 2/1968 | Armao |

(Continued)

FOREIGN PATENT DOCUMENTS

| | | |
|---|---|---|
| EP | 0315730 | 5/1989 |
| WO | 9105528 | 2/1991 |

OTHER PUBLICATIONS

Long, R., Regional Cranial Hypothermia in the Prevention of Cerebral Ischemic Damage During Carotid Occlussion, Review of Surgery, vol. 23, No. 3, May 1966, pp. 226-228.

(Continued)

*Primary Examiner* — Navin Natnithithadha
(74) *Attorney, Agent, or Firm* — Robert D. Buyan; Stout, Uxa, Buyan & Mullins, LLP

(57) ABSTRACT

The present invention provides a method and apparatus for controlling the internal body temperature of a patient. According to the present invention, a catheter is inserted through an incision into a large blood vessel of a patient. By selectively heating or cooling a portion of the catheter lying within the blood vessel, heat may be transferred to or from blood flowing within the vessel and the patient's body temperature may thereby be increased or decreased as desired. The invention will find use in treating undesirable conditions of hypothermia and hyperthermia, or for inducing a condition of artificial hypothermia when desired. The method and system further provide for the cooling of initially hypothermic patients whose blood or body temperature has been warmed above the desired target level and the warming of initially hyperthermic patients whose blood or body temperature has been cooled below the desired target temperature.

35 Claims, 11 Drawing Sheets

(56) References Cited

U.S. PATENT DOCUMENTS

| | | |
|---|---|---|
| 3,425,419 A | 2/1969 | Dato |
| 3,726,283 A | 4/1973 | Dye et al. |
| 3,788,328 A | 1/1974 | Alley et al. |
| 3,901,224 A | 8/1975 | Bucalo |
| 3,995,617 A | 12/1976 | Watkins et al. |
| 4,014,317 A | 3/1977 | Bruno |
| 4,038,519 A | 7/1977 | Foucras |
| 4,111,209 A | 9/1978 | Wolvek et al. |
| 4,246,932 A | 1/1981 | Raines |
| 4,298,006 A | 11/1981 | Parks |
| 4,378,797 A | 4/1983 | Osterholm |
| 4,445,500 A | 5/1984 | Osterholm |
| 4,445,886 A | 5/1984 | Osterholm |
| 4,470,407 A | 9/1984 | Hussein |
| 4,540,402 A | 9/1985 | Aigner |
| 4,661,094 A | 4/1987 | Simpson |
| 4,662,383 A | 5/1987 | Sogawa et al. |
| 4,672,962 A * | 6/1987 | Hershenson ............... 606/28 |
| 4,686,085 A | 8/1987 | Osterholm |
| 4,701,166 A | 10/1987 | Groshong et al. |
| 4,705,501 A | 11/1987 | Wigners et al. |
| 4,748,979 A | 6/1988 | Hershenson |
| 4,750,493 A | 6/1988 | Brader |
| 4,754,752 A | 7/1988 | Ginsburg et al. |
| 4,769,005 A | 9/1988 | Ginsburg et al. |
| 4,804,358 A | 2/1989 | Karcher et al. |
| 4,819,655 A | 4/1989 | Webler |
| 4,840,617 A | 6/1989 | Osterholm |
| 4,857,054 A | 8/1989 | Helfer |
| 4,860,744 A * | 8/1989 | Johnson et al. ............ 606/31 |
| 4,892,095 A | 1/1990 | Nakhgevany |
| 4,892,519 A | 1/1990 | Songer et al. |
| 4,899,741 A | 2/1990 | Bentley et al. |
| 4,909,252 A | 3/1990 | Goldberger |
| 4,920,963 A | 5/1990 | Brader |
| 4,941,475 A | 7/1990 | Williams et al. |
| 4,976,691 A | 12/1990 | Sahota |
| 4,995,863 A | 2/1991 | Nichols et al. |
| 5,019,075 A | 5/1991 | Spears et al. |
| 5,030,210 A | 7/1991 | Alchas |
| 5,041,089 A | 8/1991 | Mueller et al. |
| 5,092,841 A | 3/1992 | Spears |
| 5,106,360 A | 4/1992 | Ishiwara et al. |
| 5,112,301 A | 5/1992 | Fenton, Jr. et al. |
| 5,131,100 A | 7/1992 | Atwater et al. |
| 5,147,355 A | 9/1992 | Friedman et al. |
| 5,147,385 A | 9/1992 | Beck et al. |
| 5,149,321 A | 9/1992 | Klatz et al. |
| 5,151,100 A | 9/1992 | Abele et al. |
| 5,180,364 A | 1/1993 | Ginsburg |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,241,951 A | 9/1993 | Mason et al. |
| 5,248,312 A | 9/1993 | Langberg |
| 5,250,070 A | 10/1993 | Parodi |
| 5,257,977 A | 11/1993 | Eshel |
| 5,261,399 A | 11/1993 | Klatz et al. |
| 5,269,758 A | 12/1993 | Taheri |
| 5,281,213 A | 1/1994 | Milder et al. |
| 5,281,215 A | 1/1994 | Milder |
| 5,342,301 A * | 8/1994 | Saab ............... 604/103.13 |
| 5,368,591 A | 11/1994 | Lennox et al. |
| 5,383,856 A | 1/1995 | Bersin |
| 5,395,314 A | 3/1995 | Klatz et al. |
| 5,403,281 A | 4/1995 | O'Neill et al. |
| 5,423,811 A | 6/1995 | Imran et al. |
| 5,437,673 A | 8/1995 | Baust et al. |
| 5,474,080 A | 12/1995 | Hughes |
| 5,486,208 A * | 1/1996 | Ginsburg ............... 607/106 |
| 5,545,161 A | 8/1996 | Imran |
| 5,624,392 A * | 4/1997 | Saab ............... 604/43 |
| 5,658,278 A * | 8/1997 | Imran et al. ............... 606/41 |
| 5,716,386 A | 2/1998 | Ward et al. |
| 5,837,003 A | 11/1998 | Ginsburg |
| 6,149,676 A * | 11/2000 | Ginsburg ............... 607/106 |
| 6,436,131 B1 | 8/2002 | Ginsburg |
| 6,620,188 B1 | 9/2003 | Ginsburg et al. |
| 6,635,076 B1 | 10/2003 | Ginsburg |
| 6,685,733 B1 * | 2/2004 | Dae et al. ............... 607/105 |
| 6,849,083 B2 * | 2/2005 | Ginsburg ............... 607/96 |

OTHER PUBLICATIONS

White, R., et al., Profound Selective Cooling and Ischemia of Primate Brain Without Pump or Oxygenator, Surgery, vol. 66, No. 1, Jul. 1969, pp. 224-232.

Weale, F.E., The Aneroid Manometer in Peripheral Arterial Surgery, The British Journal of Surgery, vol. 56, No. 8, Aug. 1969, pp. 612-631.

Negrin, Jr., The Hypothermostat: An Instrument to Obtain Local Hypothermia of the Brain of Spinal Cord, International Surgery, Sec. 1, vol. 54, No. 2, Aug. 1970, pp. 93-106.

Safar, P., Resuscitation After Global Brain Ischemia-Anoxia, Crit. Care Med., vol. 6, No. 4, 1978, pp. 215-224.

Ping, F. et al., Protection of the Brain From Hypoxia: A Review, Canad. Anaesth. Soc. J., vol. 25, No. 6, Nov. 1978, pp. 468-473.

Safar, P., Dynamics of the Brain Resuscitation After Ischemic Anoxia, Hospital Practice, Feb. 1981,, pp. 67-72.

Gisvold, S., et al., Multifaceted Therapy After Global Brain Ischemia in Monkeys, Stroke, vol. 15, No. 5, Sep. 1984, pp. 803-812.

Leonov, Y., et al., Mild Cerebral Hypothermia During and After Cardiac Arrest Improves Neurologic Outcome in Dogs, Journal of Cerebral Blood Flow and Metabolism, vol. 10, 1990, pp. 57-70.

Minamisawa, H., et al., The Effect of Mild Hypothermia and Hypothermia on Brain Damage Following 5,10 and 15 Minutes of Forebrain Ischemia, American Neurological Association, 1990, pp. 26-33.

Tisherman, S. et al., Therapeutic Deep Hypothermic Circulatory Arrest in Dogs: A Resuscitation Modality for Hemorrahagic Shock with 'Irreparable Injury'. The Journal of Trauma, vol. 30, No. 7, Jul. 1990, pp. 836-847.

Tisherman, S., et al., Deep Hypothermic Circulatory Arrest Induced During Hemorrhagic Shock in Dogs: Preliminary Systemic and Cerebral Metabolism Studies, Current Surgery, Sep. 1990, pp. 327-330.

Leonov, Y., et al., Moderate Hypothermia After Cardiac Arrest of 17 Minutes in Dogs: Effect on Cerebral and Cardiac Outcome, Stroke, vol. 21, No. 11, Nov. 1990, pp. 1600-1606.

Sterz, F., et al., Mild Hypothermia Cardiopulmonary Resuscitation Improves Outcome After Prolonged Cardiac Arrest in Dogs, Critical Care Medicine, vol. 19, No. 3, 1991, pp. 379-389.

Tisherman, S., et al., Profound Hypothermia (<10 C) Compared With Deep Hypothermia (15 C) Improves Neurological Outcome in Dogs After Two Hours' Circulatory Arrest Induced to Enable Resuscitative Surgery, The Journal of Trauma, vol. 31, No. 8, Aug. 1991, pp. 1051-1062.

Dietrich, W., The Importance of Brain Temperature in Cerebral Injury, Journal of Neurotrauma, vol. 9 Suppl. 2, 1992, pp. S475-S485.

Ginsberg, M., et al., Therapeutic Modulation of Brain Temperature: Relevance to Ischemic Brain Injury, Cerebrovascular and Brain Metabolism Reviews, vol. 4, No. 3, 1992, pp. 189-225.

Martinez-Arizala, A., et al., Hypothermia in Spinal Cord Injury, Journal of Neurotrama, vol. 9, Suppl. 2, 1992, pp. S497-S505.

Weinrauch, V. et al., Beneficial Effect of Mild Hypothermia and Detrimental Effect of Deep Hypothermia After Cardiac Arrest in Dogs, Stroke, vol. 23, No. 10, Oct. 1992, pp. 1454-1462.

Kuboyama, K., et al., Delay in Cooling Negates the Beneficial Effect of Mild Resuscitation Cerebral Hypothermia After Cardiac Arrest in Dogs: A Prospective, Randomized Study, Crit. Care Med., vol. 21, No. 9, 1993, pp. 1348-1358.

Maher, J., et al., Hypothermia as a Potential Treatment for Cerebral Ischemia, Cerebrovascular and Brain Metabolism Reviews, vol. 5, No. 4, 1993, pp. 277-300.

Safar, P., Cerebral Resuscitation After Cardiac Arrest: Research Initiatives and Future Directions, Annals of Emergency Medicine, vol. 22, No. 2, Part 2, Feb. 1993, pp. 324-389.

Sterz, F., et al., Mild Hypothermic Cardiopulmonary Resuscitation Improves Outcome After Prolonged Cardiac Arrest in Dogs, Critical Care Medicine, vol. 19, No. 3, 1991, pp. 379-289.

Jessen, C. et al., Intravascular Heat Exchange for Conscious Goats, Pflugers Archiv European Journal of Physiology, vol. 368, 1977, pp. 263-265.

Ripstein, et al., A Technique for the Production of Hypothermia: Prelim. Report, Dept. of Surgery, Maimonides Hospital and State Univ. of NY, College of Medicine at NY, Apr. 7, 1953.

Mercer, et al., Effects of Total Body Core Cooling on Heat Production of Conscious Goats, Pflugers Archiv European Journal of Physiology, Springer-Verlag, 1978.

Onoe, M. et al., The Effect of Pulsatile Perfusion on Cerebral Blood Flow During Profound Hypothermia with Total Circulatory Arrest, Journal of Thoracic and Cardiovascular Surgery, vol. 108, Jul. 1994, pp. 119-125.

Xiao, F. et al., Peritoneal Cooling For Mild Cerebral Hypothermia After Cardiac Arrest in Dogs, Resuscitation, vol. 30, 1995, pp. 51-59.

Sessler, D., Deliberate Mild Hypothermia, Journal of Neurosurgical Anesthesiology, vol. 7, No. 1 Jan. 1995, pp. 38-46.

Capone, A. et al., Complete Recovery After Normothermic Hemorrahagic Shock and Profound Hypothermic Circulatory Arrest of 60 Minutes in Dogs, The Journal of Trauma: Injury, Infection, and Critical Care, vol. 40, No. 3, 1996, pp. 388-395.

Gisvold, S. et al., Cerebral Resuscitation From Cardiac Arrest: Treatment Potentials, Crit. Care Med., vol. 24, No. 2, Suppl., 1996, pp. S69-S80.

Kataoko, K. et al., Ischemic Neuronal Damage: How Does Mild Hypothermia Modulate It?, Molecular and Chemical Neuropathology, vol. 28, 1996, pp. 191-195.

Safar, P. et al., Selective Brain Cooling After Cardiac Arrest, Crit. Care Med., 1996, vol. 24, No. 6, pp. 911-914.

Sterz, F. et al., Mild Resuscitation Hypothermia and Outcome After Cardiopulmonary Resuscitation, Journal of Neurosurgical Anesthesiology, vol. 8, No. 1, 1996, pp. 88-96.

Wass, C. et al., Hypothermia-Associated Protection from Ischemic Brain Injury: Implications for Patient Management, International Anesthesiology Clinics: Topics in Neuroanesthesia, vol. 34, No. 4, 1996, pp. 95-111.

Safar, P. et al., Improved Cerebral Resuscitation From Cardiac Arrest in Dogs With Mild Hypothermia Plus Blood Flow Promotion, Stroke, vol. 27, No. 1, Jan. 1996, pp. 105-113.

Oku, K., et al., Mild Hypothermia After Cardiac Arrest in Dogs Does Not Affect Postarrest Multifocal Cerebral Hypoperfusion, Stroke, vol. 24, No. 10, Oct. 1993, pp. 1590-1597.

Kuboyama, K. et al., Mild Hypothermia After Cardiac Arrest in Dogs Does Not Affect Postarrest Cerebral Oxygen Uptake/Delivery Mismatching, Resuscitation, vol. 27, 1994, pp. 231-244.

Laptook, A. et al., Modest Hypothermia Provides Partial Neuroprotection for Ischemic Neonatal Brain, Pediatric Research, vol. 35, No. 4, 1994, pp. 436-442.

Salzano, R. et al., Regional Hypothermia of the Spinal Cord Protects Against Ischemic Injury During Thoracic Aortic Cross-Clamping, The Society of Thoracic Surgeons, vol. 57, 1994, pp. 65-71.

Behman, F.W., et al.; Intravascular Cooling, a Method to Achieve Controllable Hypothermia; Pflugers Archive. vol. 263, pp. 145-165 (1956) (German article with English translation).

Behman, F.W; "Heat Generation Control during Artificial Hypothermia: II. Theoretical Examinations" Pflugers Archive, Bd. 266, S. 422-446 (1958) (German article with English translation).

Behman, F.W., et al,; "Heat Generation Control during Artificial Hypothermia I: Experimental Examination of the Influence of Anesthetic Depth", Pflugers Archive, Bd. 266, S. 408-421 (1958) (German article to English translation).

Behman, F.W.; "Heat Generation Control during Artificial Hypothermia, an article about the economic problem of trembling stages", Pflugers Archive, vol. 263, pp. 166-187 (1956) (German article to English translation).

Behman, F.W,; "Regulation of heat production in experimental hypothermia of homothermal animals". Naunyn Schimiedebergs Arch Exp Pathol Pharmakol; 228 (1-2): 126-128 (1956). (German article with English translation).

Office Action dated Oct. 30, 2009 in U.S. Appl. No. 11/810,866.
File History U.S. Appl. No. 13/020,717, filed Feb. 3, 2011.
File History in U.S. Appl. No. 13/021,542, filed Feb. 4, 2011.
File History in U.S. Appl. No. 13/021,559, filed Feb. 4, 2011.
Weinrauch, V. et al., "Beneficial Effect of Mild Hypothermia and Detrimental Effect of Deep Hypothermia After Cardiac Arrest in Dogs", Stroke, vol. 23, No. 10, pp. 1454-1462, Oct. 1992.
File History in U.S Patent 6,585,692 issued Jul. 1, 2003.
File History in U.S Patent 6,716,236 issued Apr. 6, 2004.
File History in U.S Patent 6,755,851 issued Jun. 29, 2004.
File History in U.S Patent 6,942,644 issued Sep. 13, 2005.
File History in U.S. Appl. No. 11/044,997, filed Jan. 26, 2005.
File History in U.S. Appl. No. 11/129,980, filed May 16, 2005.
File History in U.S. Appl. No. 11/167,036, filed Jun. 24, 2005.
File History in U.S. Appl. No. 11/810,866, filed Jun. 6, 2007.
File History in U.S. Appl. No. 12/032,455, filed Feb. 15, 2008.

* cited by examiner

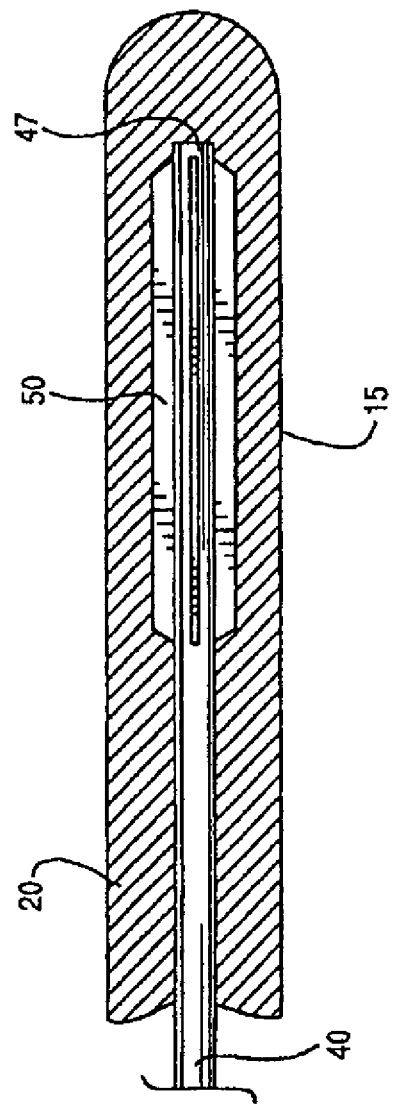
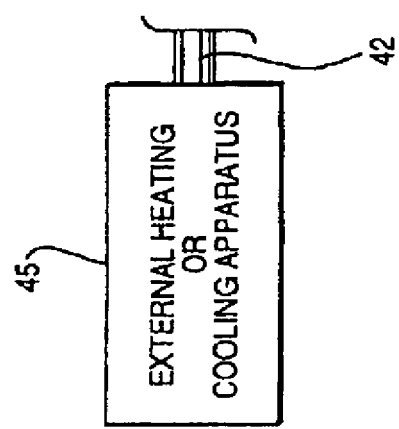
FIG. 5

| CONTROL SCHEME TO RAISE BODY TEMPERATURE | CONTROL SCHEME TO LOWER BODY TEMPERATURE |
|---|---|
| 1. MEASURE PATIENT BODY AND/OR BLOOD TEMPERATURE | 1. MEASURE PATIENT BODY AND/OR BLOOD TEMPERATURE |
| 2. MAINTAIN HEAT TRANSFER SURFACE AT 40°C TO 42°C | 2. MAINTAIN HEAT TRANSFER SURFACE AT 20°C TO 35°C |
| 3. STOP HEATING AT TARGET END POINT, e.g. BLOOD TEMPERATURE OF 42°C | 3. STOP COOLING AT TARGET END POINT, e.g. BODY TEMPERATURE OF 35°C TO 37°C |
| 4. CONTINUE MONITORING PATIENT BODY AND/OR BLOOD TEMPERATURE FOR OVERSHOOT, e.g. BLOOD TEMPERATURE EXCEEDS 43°C | 4. CONTINUE MONITORING PATIENT BODY AND/OR BLOOD TEMPERATURE FOR OVERSHOOT, e.g. BLOOD TEMPERATURE FALLS BELOW 32°C |
| 5. CONVERT TO COOLING MODE IF OVERSHOOT OCCURS | 5. CONVERT TO HEATING MODE IF OVERSHOOT OCCURS |

FIG.10

METHOD AND APPARATUS FOR CONTROLLING A PATIENT'S BODY TEMPERATURE BY IN SITU BLOOD TEMPERATURE MODIFICATION

RELATED APPLICATIONS

This patent application is a continuation of copending U.S. patent application Ser. No. 11/044,997 filed Jan. 26, 2005, which is a continuation of U.S. patent application Ser. No. 10/643,321 filed Aug. 19, 2003 and now issued as U.S. Pat. No. 6,849,083, which is a continuation of U.S. patent application Ser. No. 10/004,579 filed Dec. 4, 2001 and now issued as U.S. Pat. No. 6,635,076 which is a continuation of U.S. patent application Ser. No. 09/522,135 filed on Mar. 9, 2000 and now issued as U.S. Pat. No. 6,436,131 which is a continuation of U.S. patent application Ser. No. 09/131,081 filed Aug. 7, 1998 and now issued as U.S. Pat. No. 6,149,676 which is a division of Ser. No. 08/584,013 filed Jan. 8, 1996 and now issued as U.S. Pat. No. 5,837,033 which is a continuation of U.S. patent application Ser. No. 08/015,774 filed Feb. 10, 1993, now abandoned, the entire disclosures of which are incorporated herein by reference.

BACKGROUND OF THE INVENTION

1. Field of the Invention

The present invention relates generally to the selective modification and control of a patient's body temperature. More particularly, the present invention provides methods and apparatus for treating hypothermia or hyperthermia by inserting a catheter into a blood vessel of the patient and selectively transferring heat to or from blood flowing through the vessel.

2. Description of the Background Art

Under ordinary circumstances the thermoregulatory system of the human body maintains a near constant temperature of about 37.degree. C. (98.6.degree. F.). Heat lost to the environment is precisely balanced by heat produced within the body.

Hypothermia is a condition of abnormally low body temperature. Hypothermia can be clinically defined as a core body temperature of 35 degrees C. or less. Hypothermia is sometimes characterized further according to its severity. A body core temperature in the range from 32 degrees C. to 35 degrees C. is described as "mild" hypothermia, 30 degrees C. to 32 degrees C. is called "moderate," 24 degrees C. to 30 degrees C. is described as "severe," and a body temperature less than 24 degrees C. constitutes "profound" hypothermia. Although the above ranges provide a useful basis for discussion, they are not absolutes and definitions vary widely in the medical literature.

Accidental hypothermia results when heat loss to the environment exceeds the body's ability to produce heat internally. In many cases, thermoregulation and heat production are normal but the patient becomes hypothermic due to overwhelming environmental cold stress. This is a relatively common condition, often resulting from exposure to the elements. Hypothermia may also occur in patients exposed to mild cold stress whose thermoregulatory ability has been lessened due to injury or illness. For example, this type of hypothermia sometimes occurs in patients suffering from trauma or as a complication in patients undergoing surgery.

Hypothermia of either type is a dangerous condition which can have serious medical consequences. In particular, hypothermia interferes with the ability of the heart to pump blood. Hypothermia may be fatal for this reason alone. Additionally, low body temperature seriously interferes with the enzymatic reactions necessary for blood clotting. This sometimes results in bleeding that is very difficult to control, even when normal clotting factor levels are present. These effects and other adverse consequences of hypothermia lead to drastically increased mortality rates both among victims of trauma and in patients undergoing surgery.

Simple methods for treating hypothermia have been known since very early times. Such methods include wrapping the patient in blankets, administering warm fluids by mouth, and immersing the patient in a warm water bath. While these methods are very effective for mild hypothermia, more intrusive methods have been developed for treating severe and profound cases of hypothermia. In particular, methods have been devised to effect direct heating of a patient's blood. Most commonly, blood is withdrawn from patient's circulation, passed through external warming equipment, and reinfused back into the patient. Alternatively, the use of heated catheters has been proposed, where a catheter having a heating element near its distal end is inserted into the patient's vasculature and heat directly transferred into the patient's circulating blood.

While the direct heating of patient blood can be highly effective, even in treating severe and profound cases of hypothermia, it has been observed by the inventor herein that the excess transfer of heat can cause the patient's temperature to rise above normal body temperature, resulting in hyperthermia. Hyperthermia can occur, for example, when a hypothermic patient's metabolism begins to produce substantial amounts of heat at the same time heat is being transferred directly to the blood.

It would therefore be desirable to provide methods for treating hypothermia which further provide for treatment of accidental or incidental hyperthermia. In particular, it would be desirable to develop systems and methods for transferring heat to the blood where heat can be optionally removed if the patient blood or body temperature exceeds a target level. Such methods and devices will preferably employ a catheter for direct heat transfer into circulating blood, but could also be useful with methods where blood is heated externally from the patient's body. Such systems and methods should further be useful for the treatment of patients who are initially hyperthermic, where the methods and systems provide for initial cooling of the blood and optional heating of the blood should the patient blood or body temperature fall below a target temperature.

SUMMARY OF THE INVENTION

The present invention provides apparatus and methods for restoring normal body temperature in patients initially suffering from hypothermia or hyperthermia. The apparatus includes a catheter and a control unit which together permit selective heating and cooling of the patient's circulating blood. For hypothermic patients, the method will provide for initially heating the blood until a target blood or body temperature has been restored. Heating will be stopped after reaching the target temperature. Even after the heating has been stopped, however, the patient's blood and/or body temperature will continue to be monitored to assure that the blood or body temperature does not overshoot the target. As discussed above, an initially hypothermic patient can become hyperthermic if the total amount of heat experienced from both patient metabolism and external heating exceeds that necessary to restore normal body temperature. In the case of patients entering hyperthermia, the method of the present invention provides for cooling the patient's blood, usually using the same intravascular catheter or other apparatus which has been used for heating.

In the case of initially hyperthermic patients, the method of the present invention relies on cooling the patient's blood in order to reduce the blood and body temperature. Cooling will stop after a target temperature has been reached. The patient's blood and/or body temperature will continue to be monitored, however, and should the patient enter hypothermia, normal body temperature can then be restored by introducing an appropriate amount of heat to the circulating blood.

According to a first aspect of the present invention, a system for restoring normal body temperature to a patient comprises an intravascular catheter having at least one heat transfer surface, a temperature sensor, and a control unit connectable to the temperature sensor and the catheter. The control unit selectively transfers heat to or from the at least one heat transfer surface in order to achieve a desired target blood or body temperature. The intravascular catheter may comprise a single heat transfer surface for both heat generating and heat absorption, but will usually comprise both a heat-generating surface and a separate heat-absorbing surface. The heat-generating surface will typically comprise a resistance heater, such as a wire coil, and the heat-absorbing surface will typically comprise a metal foil wrapped around the catheter, typically having an exposed area of at least about 2 $cm^2$. In such cases, the control unit may comprise an electrical current source connectable to the resistance heater and a thermal electric cooler connectable to the metal foil. In an alternative construction, the catheter may include at least one flow lumen which permits flow of a heat exchange medium within the catheter past the heat transfer surface. The control unit will then include a heater, a cooler, and a controller for selectively activating the heater or cooler to transfer heat to the heat exchange medium in order to restore normal body temperature to the patient. The heater may be an electrical resistance heater and the cooler may be a thermoelectric cooler.

The temperature sensor will typically be on the catheter and measure the blood temperature. Alternatively or additionally, temperature sensor(s) may be separately attachable to the patient to measure body temperature.

In a second aspect of the present invention, a catheter for restoring normal body temperature to a patient by selectively transferring heat to or from a patient's blood flow comprises a catheter body having a proximal end and a distal end. The distal end is insertable into a blood vessel, and the heat-generating heat exchange surface and a heat-absorbing heat exchange surface are both disposed near the distal end of the catheter body. Typically, the catheter body will have a length in the range from about 15 cm to 50 cm and a diameter in the range from 1 mm to 5 mm. The heat-generating heat transfer surface will usually comprise an electrical resistance heater, and the catheter will further comprise a connector which connects the resistance heater to an external current source. The heat-absorbing heat transfer surface will typically comprise a metal foil wrapped around the catheter body, and a heat-conductive element will extend through the catheter body to near the proximal end to permit the heat-absorbing foil to be connected to a cooler in a separate control unit. The metal foil heat-absorbing surface will typically have an area of at least 2 $cm^2$, usually being from 4 $cm^2$ to 80 $cm^2$. The heat-conductive element could be either a continuation of the metal foil surface (preferably being insulated in portions which will not lie within the blood circulation), or alternatively could be a metal core composed of a heat-conductive material.

According to the method of the present invention, normal body temperatures are restored to a patient by selectively introducing heat to the patient's blood flow for hypothermic patients or removing heat from the blood flow for hyperthermic patients. Usually, the heat will be introduced or removed via an intravascular catheter which is connected to an external control unit. Alternatively, the method of the present invention will also comprise the direct extracorporeal heating and cooling of the blood. A temperature characteristic of the patient is monitored, typically being blood temperature and/or body temperature. If the temperature characteristic indicates that initially hypothermic patients have or are about to become hyperthermic, then heat will be removed from the circulating blood to restore normal body temperature. Similarly, if the monitored temperature characteristic indicates that initially hypothermic patients are about to become hyperthermic, then heat will be removed from the blood of those patients until normal body temperature has been restored.

The preferred intravascular catheters will be inserted into a blood vessel, usually being the femoral artery or vein, or the jugular artery or vein. The heat-introducing step comprises introducing heat at a rate between 10 W and 500 W, usually between 50 W and 250 W, while the heat removing step comprises removing heat at a rate from 1 W to 100 W. Preferably, the catheter and system described above will be employed.

For initially hypothermic patients, the temperature characteristic will usually be blood temperature, and the target blood temperature, i.e., temperature at which heating is stopped, will be 36.9 degrees C. Should the blood temperature exceed 39 degrees C., then cooling will commence. For initially hyperthermic patients, the preferred temperature characteristic will be blood temperature, and the target temperature at which cooling will be stopped will be about 36.9 degrees C. Should the blood continue to cool, typically to a temperature of 36 degrees C. or below, then blood heating will commence. Is should be appreciated, however, that these temperature targets are nominal objectives, and the methods of the present invention can be practiced with target temperatures which differ somewhat from those just set forth.

BRIEF DESCRIPTION OF THE DRAWINGS

FIG. 5 depicts a catheter in which heat is transferred down a thermally conductive shaft between the distal end of the catheter and heating or cooling apparatus at the proximal end of the shaft;

FIG. 10 illustrates the control schemes for raising body temperature in a patient suffering from hypothermia and lowering body temperature in a patient suffering from hyperthermia, respectively.

DESCRIPTION OF THE PREFERRED EMBODIMENT

The present invention provides methods and apparatus for selectively modifying and controlling a patient's body temperature by warming or cooling the patient's blood, usually using an intravascular catheter in situ. According to the preferred method of the present invention, the catheter is inserted through a puncture or incision into a blood vessel in the patient's body. By warming or cooling a portion of the catheter, heat may be transferred to or from blood flowing within the vessel and the patient's body temperature may thereby be increased or decreased as desired. During the procedure, the patient's blood and/or body core temperature may be independently monitored and treatment may continue until the patient's blood and/or body core temperature approaches the desired level, usually the normal body temperature of about 37 degrees C. Such methods will find use in treating undesirable conditions of hypothermia and hyperthermia and may also be used to induce an artificial condition of hypothermia when desired, e.g., to temporarily reduce a patient's need for oxygen. In such a case, the patient's temperature may be reduced several degrees Celsius below the normal body temperature.

In treating conditions of hypothermia and hyperthermia there is the possibility that the patient's core body temperature will "overshoot" the target normal body temperature. The body's metabolic response to the external heating or cooling being applied, as described above, can result in overcompensation of the initial condition. In particular, when heating the patient's body to treat hypothermia, the body's own heat generation arising from internal metabolic processes may raise the body temperature in an unpredictable manner, resulting in a body temperature that can rise well above normal body temperature. In such cases, the present invention provides for a reversal of the transfer of heat from or to the patient's blood. In the case of an uncontrolled temperature rise, the system of the present invention will be switched so that heat will be withdrawn from the circulating blood. Conversely, in the case of overcooling of the patient's body, the system will be switched so that heat will be introduced to the patient.

Figure 1:
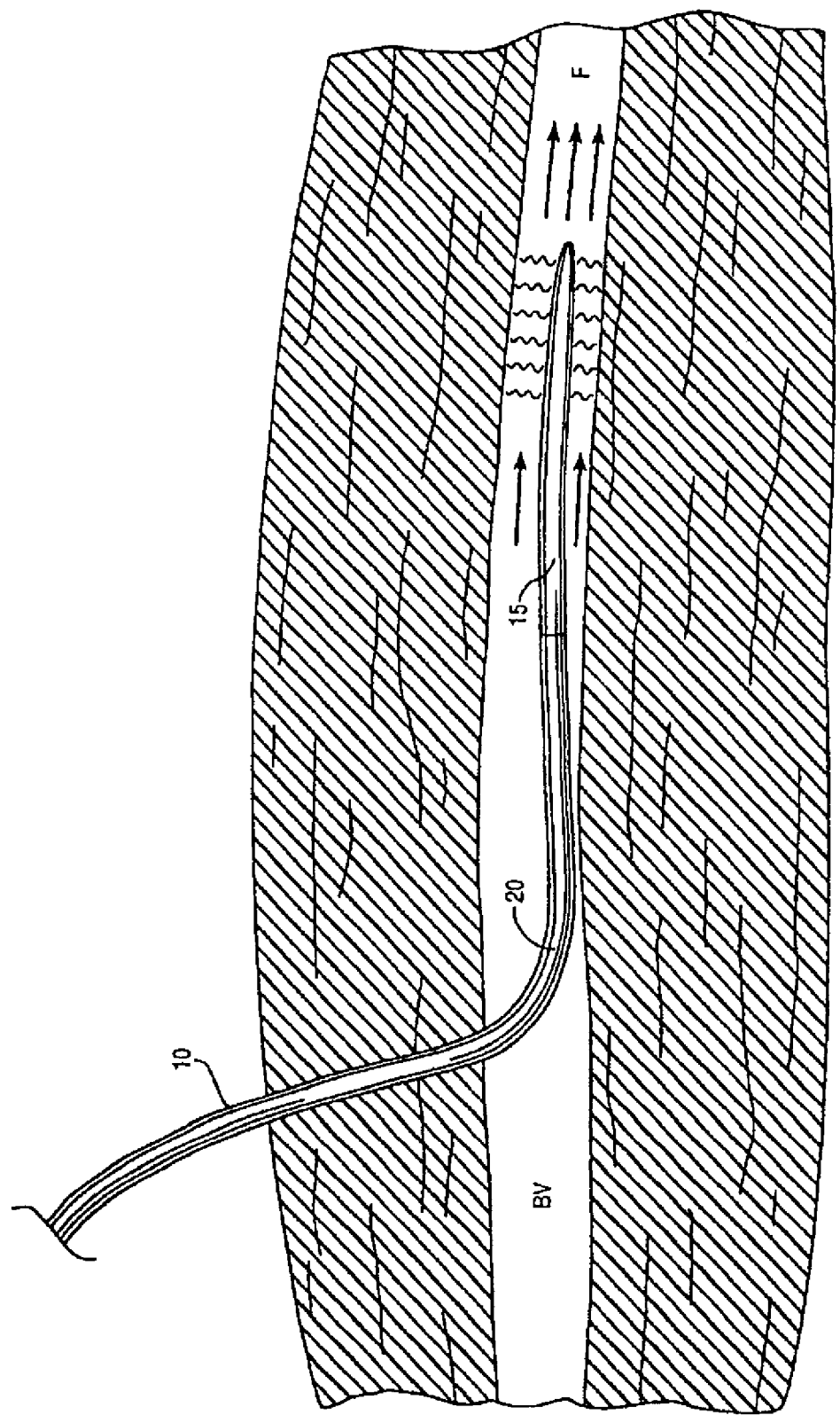
FIG. 1 depicts a catheter according to the present invention inserted percutaneously into a blood vessel of a patient.

FIG. 1 depicts a distal end 15 of a catheter 10 according to the present invention. The catheter has been inserted through the patient's skin into a blood vessel BV. Blood How through the vessel is indicated by a set of flow arrows F. Preferably, the catheter will be inserted into a relatively large blood vessel, e.g., the femoral artery or vein or the jugular vein. Use of these vessels is advantageous in that they are readily accessible, provide safe and convenient insertion sites, and have relatively large volumes of blood flowing through them. In general, large blood flow rates facilitate quicker heat transfer into or out of the patient.

For example, the jugular vein may have a diameter of about 22 French, or a bit more than 7 millimeters (1 French=0.013 inches=0.33 mm). A catheter suitable for insertion into a vessel of this size can be made quite large relative to catheters intended for insertion into other regions of the vascular system. Atherectomy or balloon angioplasty catheters are sometimes used to clear blockages from the coronary artery and similar vessels. These catheters commonly have external diameters in the range between 2 and 8 French.

In contrast, it is anticipated that a catheter according to the present invention will typically have an external diameter of about 10 French or more, although this dimension may obviously be varied a great deal without departing from the basic principles of the claimed invention. It is desirable that the catheter be small enough so that the puncture site can be entered using the percutaneous Seldinger technique, a technique well known to medical practitioners. To avoid vessel trauma, the catheter will usually be less than 12 French in diameter upon insertion. Once in the vessel however, the distal or working end of the catheter can be expanded to any size so long as blood flow is not unduly impeded.

Additionally, the femoral artery and vein and the jugular vein are all relatively long and straight blood vessels. This will allow for the convenient insertion of a catheter having a temperature controlled region of considerable length. This is of course advantageous in that more heat may be transferred at a given temperature for a catheter of a given diameter if the length of the heat transfer region is increased.

Techniques for inserting catheters into the above mentioned blood vessels are well known among medical personnel. Although the method of the present invention will probably be most commonly employed in a hospital, the procedure need not be performed in an operating room. The apparatus and procedure are so simple that the catheter may be inserted and treatment may begin in some cases even in an ambulance or in the field.

The distal end 15 of the catheter may be heated or cooled as desired and held at a temperature either somewhat above or somewhat below the patient's body temperature. Blood flowing through the vessel will thereby be warmed or cooled. That blood will be circulated rapidly throughout the patient's circulatory system. The beneficial effect of warming or cooling the patient's blood in the vicinity of the catheter will thereby be spread very quickly throughout the entire body of the patient.

Figure 2:
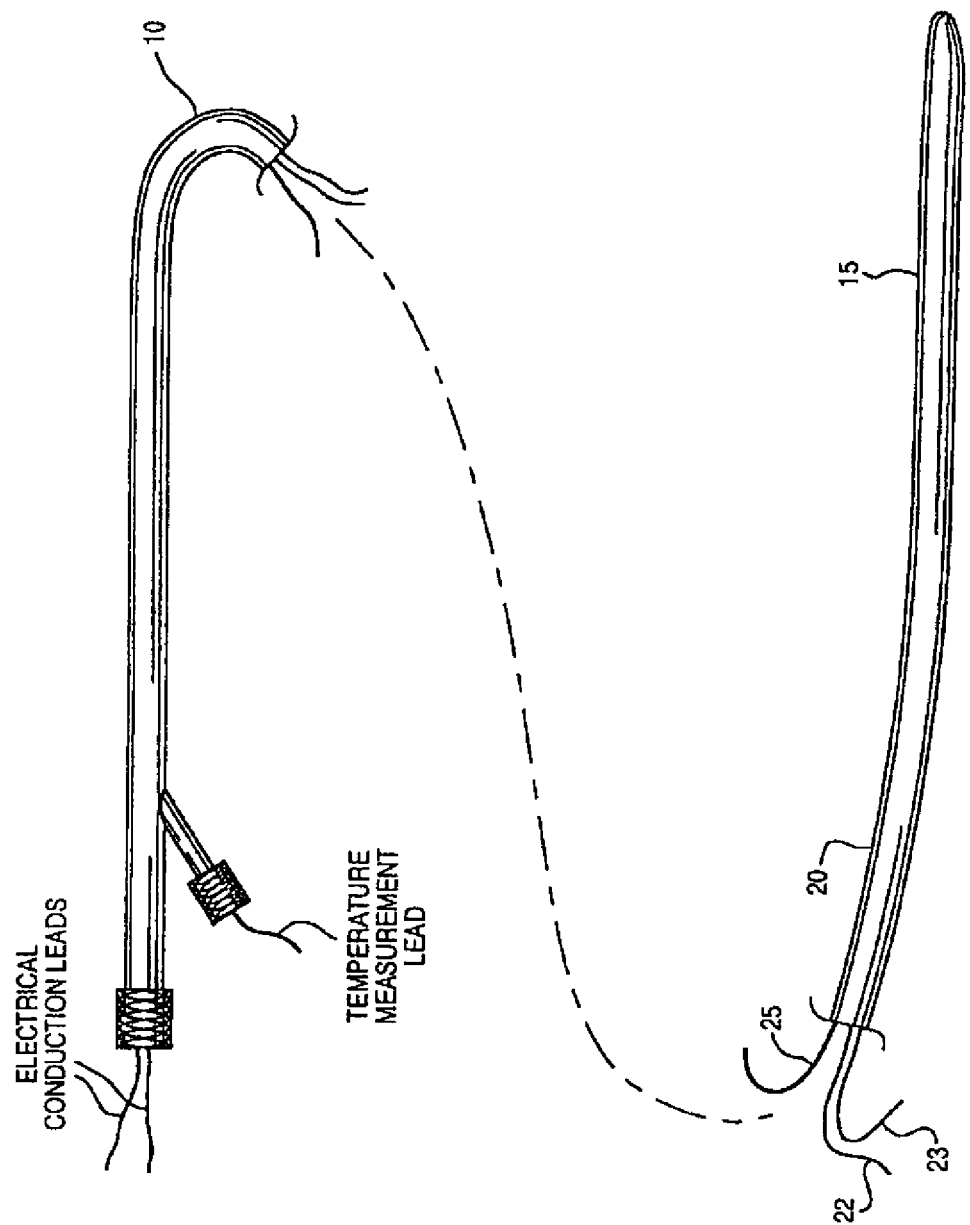
FIG. 2 depicts a catheter suitable for increasing the temperature of a patient's blood by electrical resistance heating.
Figure 3:
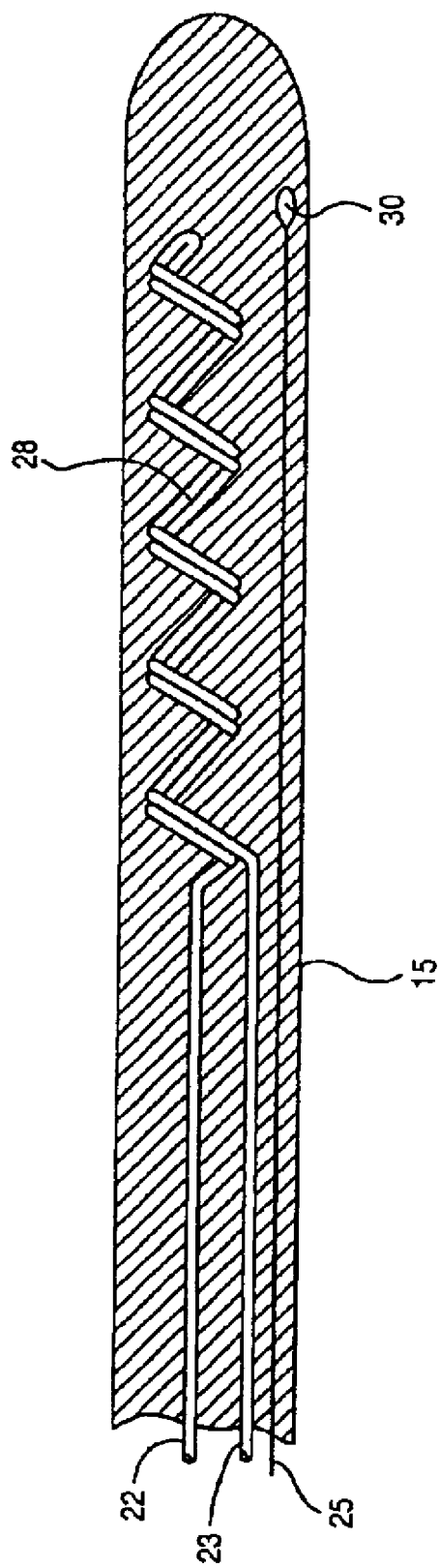
FIG. 3 depicts the distal end of a catheter having a resistance heating element and a temperature sensor.

FIGS. 2 and 3 depict a catheter suitable for treating hypothermia by increasing the temperature of a patient's blood. As depicted in FIG. 2, the catheter has a preferably flexible catheter body 20. Disposed within the catheter body are a pair of electrical conduction leads 22 and 23 and a temperature measurement lead 25.

Electrical conduction leads 22 and 23 are connected to a resistance heating element 28, as depicted in FIG. 3. Electrical current provided by a power source (not shown) is converted to heat within the heating coil. That heat warms distal end 15 of the catheter and is thereby transferred to blood flowing through the vessel.

Temperature measurement lead 25 is connected to a temperature sensor 30. The temperature sensor facilitates the control of current flow through the heating coil. It is important to closely monitor the temperature of the distal end of the catheter and thus the flow of heat into the patient's blood. Care must be taken not to overheat the blood while still providing an adequate rate of heat transfer into the patient. The provision of a sensitive temperature sensor at the distal end of the catheter will help to achieve this goal.

Figure 4:
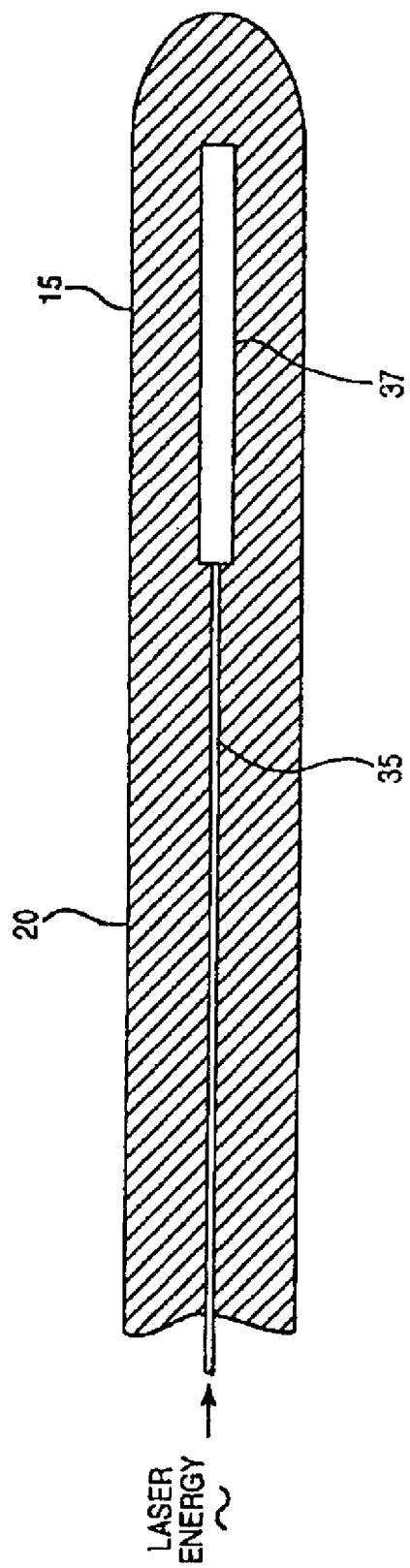
FIG. 4 depicts the distal end of a catheter having an optical wave guide and an optical diffusing tip for converting laser energy into heat.

FIG. 4 depicts an alternate embodiment of a catheter having means for transferring energy from an external power source to distal end 15 of catheter body 20. In this embodiment, laser energy from a laser light source (not shown) is transmitted along optical wave guide 35. The wave guide directs the laser energy into optical diffusing tip 37, which converts the laser energy to heat. From diffusing tip 37, the heat radiates outward into distal end 15 of the catheter and from there into the patient's blood stream.

FIG. 5 depicts another catheter suitable for practicing the present invention. This embodiment has a thermally conductive shaft 40 running the length of catheter body 20. Shaft 40 is made of a metal or other material having a high thermal conductivity. By heating or cooling the proximal end 42 of shaft 40 with an external heating or cooling apparatus 45, heat will be caused to flow either into or out of the distal end 47 of the shaft. In the embodiment depicted, the distal end of the shaft is fitted with heat transfer vanes 50, which add to the surface area of the shaft and thereby promote more effective heat transfer between the catheter and the patient's blood stream.

Figure 6:
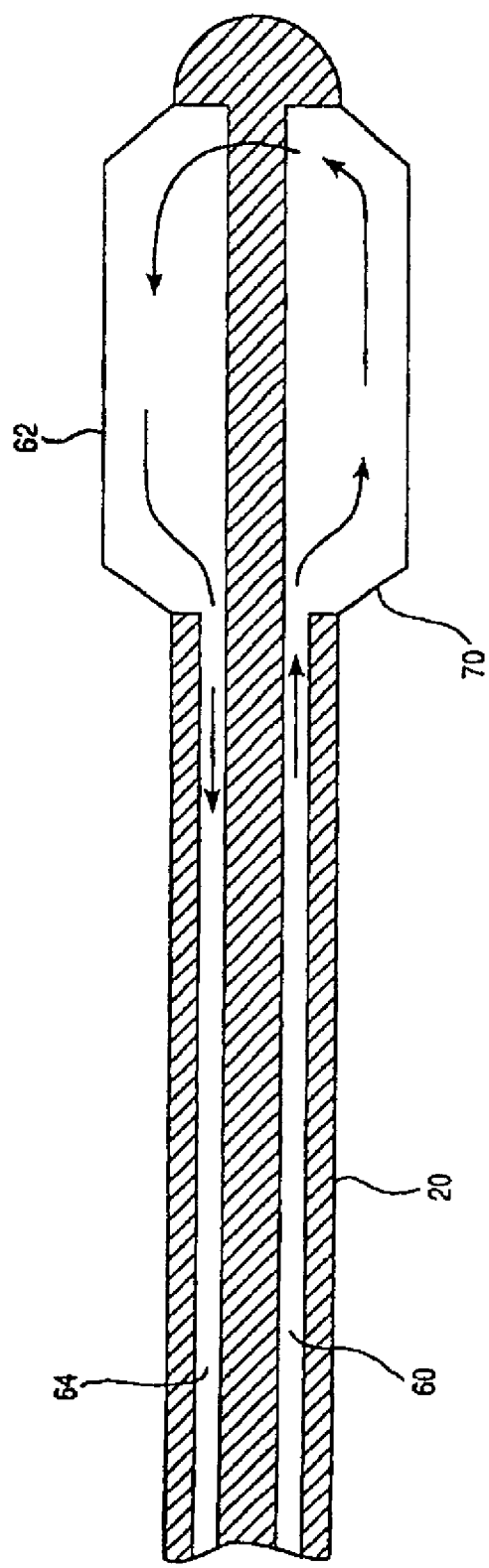
FIG. 6 depicts a catheter in which a heated or cooled fluid flows through a balloon, which provides for an increased surface area at the distal end.

FIG. 6 depicts still another means for transferring heat to or from the distal end of a catheter. In this embodiment, catheter body 20 has two lumens running through it. Fluid flows from the proximal end of the catheter through in-flow lumen 60, through a heat transfer region 62, and back out through out-flow lumen 64. By supplying either warmed or cooled fluid through inflow lumen 60, heat may be transferred either to or from the patient's blood stream.

In the embodiment depicted, heat transfer region 62 is in the form of a balloon 70. Use of a balloon will be advantageous in some embodiments to provide an increased surface area through which heat transfer may take place. Balloon inflation is maintained by a pressure difference in the fluid as it flows through in-flow lumen 60 and out-flow lumen 64. The balloon should be inflated to a diameter somewhat less than that of the inside diameter of the blood vessel so as not to unduly impede the flow of blood through the vessel.

Figure 7:
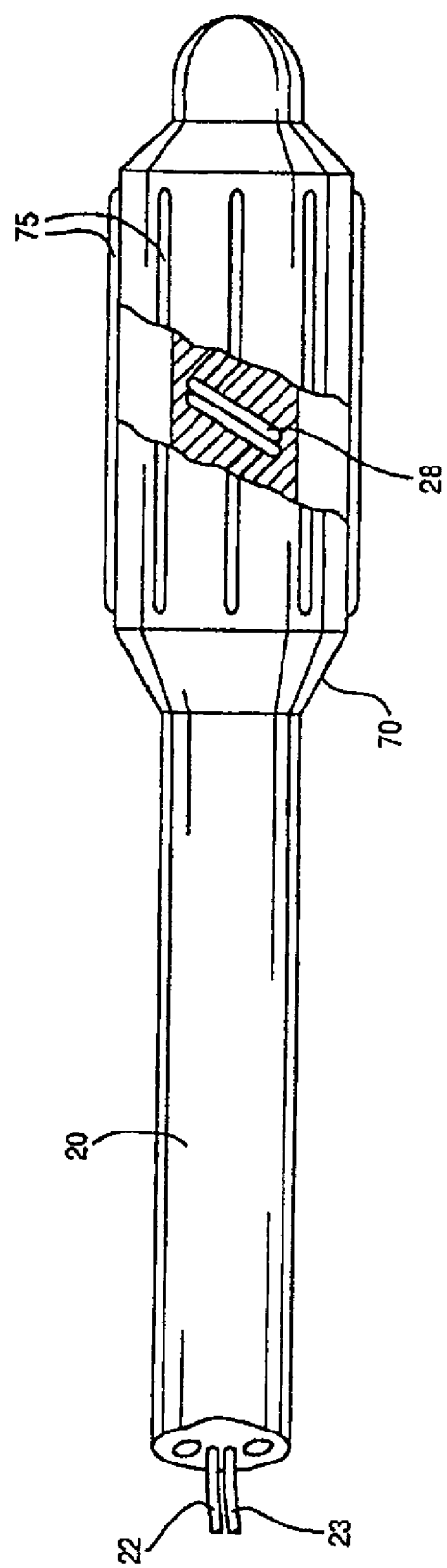
FIG. 7 depicts a catheter having a resistance heating element at its distal end and a balloon having longitudinal ribs to further increase the heat transfer surface area.
Figure 8A:
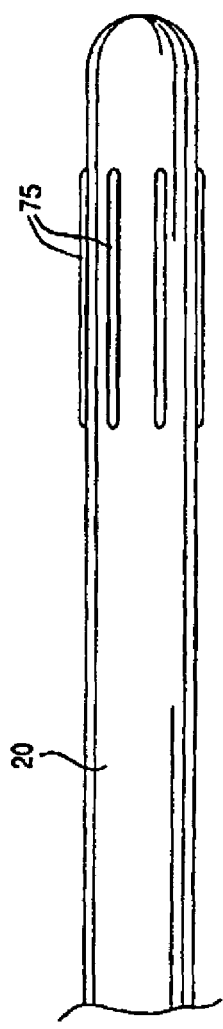
FIG. 8A depicts a catheter having longitudinal fins at the distal end of the catheter body.
Figure 8B:
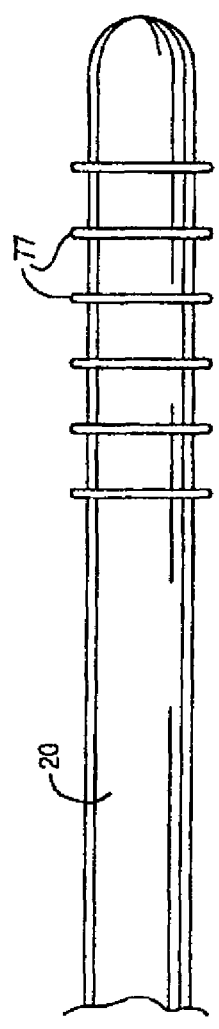
FIG. 8B depicts a catheter having radial ribs at the distal end of the catheter body.
Figure 8C:
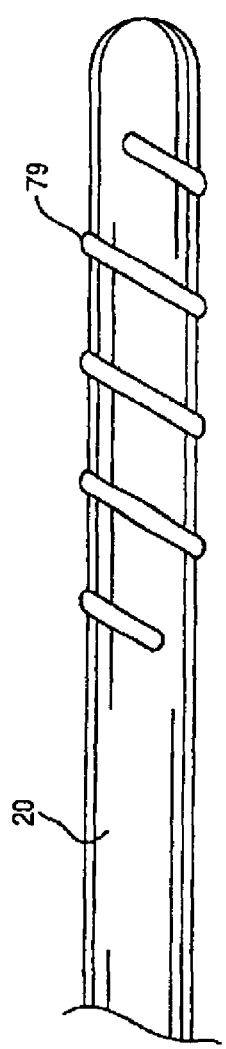
FIG. 8C depicts a catheter having a spiral fin to increase the heat transfer area at the distal end of the catheter.

FIG. 7 depicts a catheter having an internal resistance heating element 28 and a balloon 70, which is shown inflated. In this embodiment, the increased surface area provided by the inflated balloon is further augmented by the presence of a set of longitudinal fins 75 on the surface of the balloon. Alternatively, longitudinal tins 75, radial ribs 77, or one or more spiral fins 79 may be disposed directly on the body 20 of a catheter as shown in FIGS. 8A, 8B and 8C. Ordinarily, longitudinal ribs will be most advantageous because they restrict blood flow through the vessel less than other configurations. In fact, these ribs insure that the balloon will not block the flow of blood through the vessel because a flow path will always be maintained (between the ribs) regardless of how much the balloon is inflated.

Inclusion of a balloon on a catheter employing resistance heating allows for designs in which current is conducted through the fluid which fills the balloon. The catheter depicted in FIG. 9 has a catheter body 20 about which is disposed an inflatable balloon 70. The balloon is inflated by injecting a suitable fluid into the balloon through central balloon inflation lumen 80. In this embodiment, current flows from an external source of electrical power (not shown) through conduction wires 82 and 84 to electrodes 86 and 88.

A suitable fluid will allow current to flow between electrodes 86 and 88. Common saline solution, for example, contains dissolved ions which can serve as charge conductors. Electrical resistance within the fluid will cause the fluid to be heated, thus providing the desired warming of the catheter. The amount of warming will be dependant upon the voltage between the electrodes, the distance between them, and the resistivity of the fluid. The relation between these quantities is fairly simple; one skilled in the art will have no difficulty selecting appropriate values.

Figure 9:
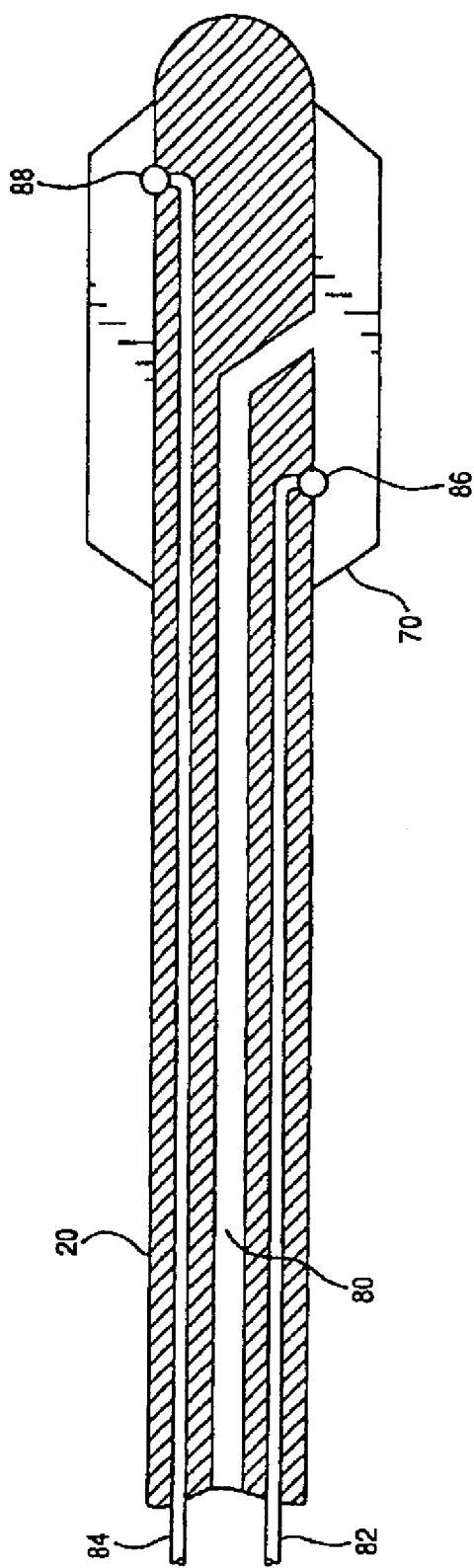
FIG. 9 illustrates a catheter having a resistance heater which heats a fluid filling a balloon. Current flows through the fluid from a pair of conduction wires embedded in the catheter body.

Resistance heating catheters like those depicted in FIGS. 3, 7 and 9 may use DC or low frequency AC power supplies. However, it may be desirable to use a higher frequency power supply. For example, it is known that the risk of adverse physiological response or electrocution response may be lessened at frequencies within the range of about 100 kilohertz to 1 megahertz. Power supplies that operate at these frequencies are commonly referred to as radio-frequency, or RF, power supplies.

A catheter according to the present invention should be designed to optimize the rate of heat transfer between the catheter and blood flowing through the vessel. While a large surface area is desirable in order to maximize heat transfer, care must be taken so that the catheter does not unduly restrict blood flow through the vessel. Furthermore, the temperature of the catheter should be carefully controlled to prevent undesirable chemical changes within the blood. This is especially important when applying heat to the blood as blood is readily denatured by even moderately high temperatures. The exterior temperature of a catheter for warming blood should generally not exceed about 42.degree. C.-43.degree. C.

It is estimated that a catheter whose surface temperature is controlled between 37 degrees C. and 42 degrees C. will provide a body core warming rate of approximately one to two degrees Celsius per hour in a patient starting out with severe hypothermia. This estimate is highly dependant on a number of factors including the rate of blood flow through the vessel, the initial body temperature of the patient, the external surface area of the catheter through which heat is conducted, etc. The actual rate achieved may vary substantially from the above estimate.

The above estimate provides a starting point for a rough estimate as to the level of power transferred from the catheter to the patient's body and therefore of the size of the power supply required by the system. Regardless of the exact means of power transmission chosen, resistance heating coil, laser and diffusing tip, direct conduction or fluid circulation, an appropriate power supply will be required to provide heat to the system.

The sum of heat entering and leaving a patient's body can be written as:

$$\Delta H = H_c + H_i - H_e$$

where $\Delta H$ is the sum of all heat transferred, $H_c$ is the heat transferred from the catheter to the patient. $H_i$ the heat produced by the patient internally, and $H_e$ the heat lost from the patient to the environment. If one assumes, as will ordinarily be the case in a healthy patient, that the body's internal thermoregulatory system will produce just enough heat to offset heat lost to the environment, then the equation is made simple:

$$\Delta H = H_c$$

The above equation can be written in terms of the change in the patient's internal body temperature over time as follows:

$$mc(\Delta T/\Delta t) = (\Delta H_c/\Delta t)$$

where m is the body mass of the patient, c is the specific heat of the patient's body, $(\Delta T/\Delta t)$ is the time rate of change of the patient's internal body temperature, $(\Delta H_c/\Delta t)$ is the time rate of heat delivery from the catheter to the patient.

If one assumes a patient having a body mass of 75 kilograms and a specific heat of 4186 joules/° C.-kg (assumes the specific heat of the human body to be the same as that of water, the actual value will be somewhat different), then a warming rate of 1 degree C. per hour (3600 seconds) will require the catheter to transfer heat to the patient at a rate of about 87 watts (1 watt=1 joule/sec).

However, as an estimate of the desirable size of a power supply to be used with a catheter of the present invention, this estimate is almost certainly too low. This is true for a number of reasons. First, it was assumed for the sake of convenience that the patient's internal system would produce an amount of heat equal to that lost to the environment. In a hypothermic patient this will obviously not be the case. Almost by definition, hypothermia occurs when a person's ability to produce heat internally is overwhelmed by heat lost to the environment. The catheter will have to make up the difference so the power level required will need to be greater for that reason alone.

Additionally, the above estimate does not allow for power losses between the power supply and whatever warming means is utilized. Such losses could include resistance losses in electrical transmission lines between the power supply and a resistance heating element, inherent inefficiencies and other losses in a system having a laser and a diffusing tip, heat losses along a thermally conductive shaft or fluid circulation lumen, and the like. Any such losses which do occur will need to be compensated for by additional power supply capacity.

Furthermore, it would be undesirable to limit the performance of a catheter according to the present invention by limiting the size of the power supply used. It would be preferable instead to use a power supply capable of providing power considerably in excess of that actually needed and then controlling the delivery of that power according to the measured temperature of the catheter itself. As mentioned previously, this can be readily accomplished by including a sensitive temperature sensor within the body of the catheter. Nevertheless, the above calculation can be used as a useful estimate of the likely lower bound for sizing a power supply for use in a catheter according to the present invention.

An alternative estimate can be made by comparing the likely performance of the various embodiments described herein with the power requirements for the external blood warming apparatus presently known. Such external warming apparatus generally requires a supply of power on the order of 1000-1500 watts and sometimes more. A device according to the present invention will most likely require considerably less power than that. First, the present invention requires no external pump to circulate the blood; this function is provided by the patient's own heart. Accordingly, no power is needed to drive such a pump. Secondly, the present invention is considerably less complicated than external blood warming systems. Known systems circulate the blood over a relatively lengthy path from the patient, through the warming element, and back into the patient. It is expected that more heat is lost over this lengthy path than will be lost in any device according to the present invention.

Thus, the power required by external blood circulation and warming systems of the type previously known can be used as a rough estimate of the likely upper limit for power required by a system according to the present invention. It is most likely that such a system will best be equipped with a power supply having a capacity somewhere between the two rough estimates described above. It is therefore contemplated that a suitable power supply will be capable of providing peak power somewhere in the range between 100 and 1500 watts, probably being in the range between 300 and 1000 watts. The ranges specified are an estimate of suitable peak power capability. The power supply will most commonly be thermostatically controlled in response to a temperature sensor in the body of the catheter. The actual effective power transmitted to the patient will therefore typically be much less than the peak power capacity of the system power supply.

With respect to a catheter for cooling, the temperature and power constraints are not as limiting as is the case in a catheter for warming blood. Care should merely be taken to avoid freezing the blood or inducing shock to the patient from too rapid cooling.

Blood is essentially water containing a number of suspended and dissolved substances. As such, its freezing point is somewhat below 0.degree. C. However, a catheter adapted to cool blood in a hyperthermic patient or to induce an artificial hypothermia will usually not be operated at temperatures that low. It is presently contemplated that the external surface of such a catheter may be held in the range between about 20 degrees C. and 24 degrees C., although the actual temperature could vary between about 0 degrees C. and the patient's current body temperature (somewhat in excess of 37 degrees C.).

Various embodiments of apparatus suitable for practicing the methods of the present invention have been described. Other embodiments and modifications will occur to those skilled in the art. For example, various means for heat transfer, e.g., resistance, including radio frequency, heating; laser energy: pumped fluids; etc. may be combined with various means for increasing the effective heat transfer surface area, e.g., balloons, fins, ribs, etc. to optimize the function of a device according to the present invention. Also, a temperature sensor will typically be used although for ease of illustration such a sensor is not depicted in all of the embodiments described. Furthermore, although most of the figures depict embodiments in which only a limited portion of the catheter is temperature controlled, no reason exists to prevent warming or cooling substantially the whole length of the catheter.

Broadly stated, the present invention provides a method for modifying a patient's body temperature by controlling the temperature of a catheter inserted into a blood vessel of the patient. Although several illustrative examples of means for practicing the invention are described above, these examples are by no means exhaustive of all possible means for practicing the invention. The scope of the invention should therefore be determined with reference to the appended claims, along with the full range of equivalents to which those claims are entitled.

The present invention thus provides methods for both raising the body temperature of initially hypothermic patients and lowering the body temperature of patients who are initially hyperthermic or for whom the body temperature is to be lowered below normal for some other purpose. In all cases, it is possible that the target body temperature will be inadvertently exceeded due to an uncontrollable physiologic response of the patient, e.g., initially hypothermic patients may become hyperthermic and initially hyperthermic patients may become hypothermic. In such cases, the present invention specifically provides for reversing the heat transfer process so that patients passing into hyperthermia can be immediately cooled and patients passing into hypothermia can be immediately warmed. The control schemes for both warming initially hypothermic and cooling initially hyperthermic patients are set forth in FIG. 10. The initial, target, and overshoot temperatures for both initially hyperthermic and initially hypothermic patients are set forth in Table 1 below.

Figure 11:
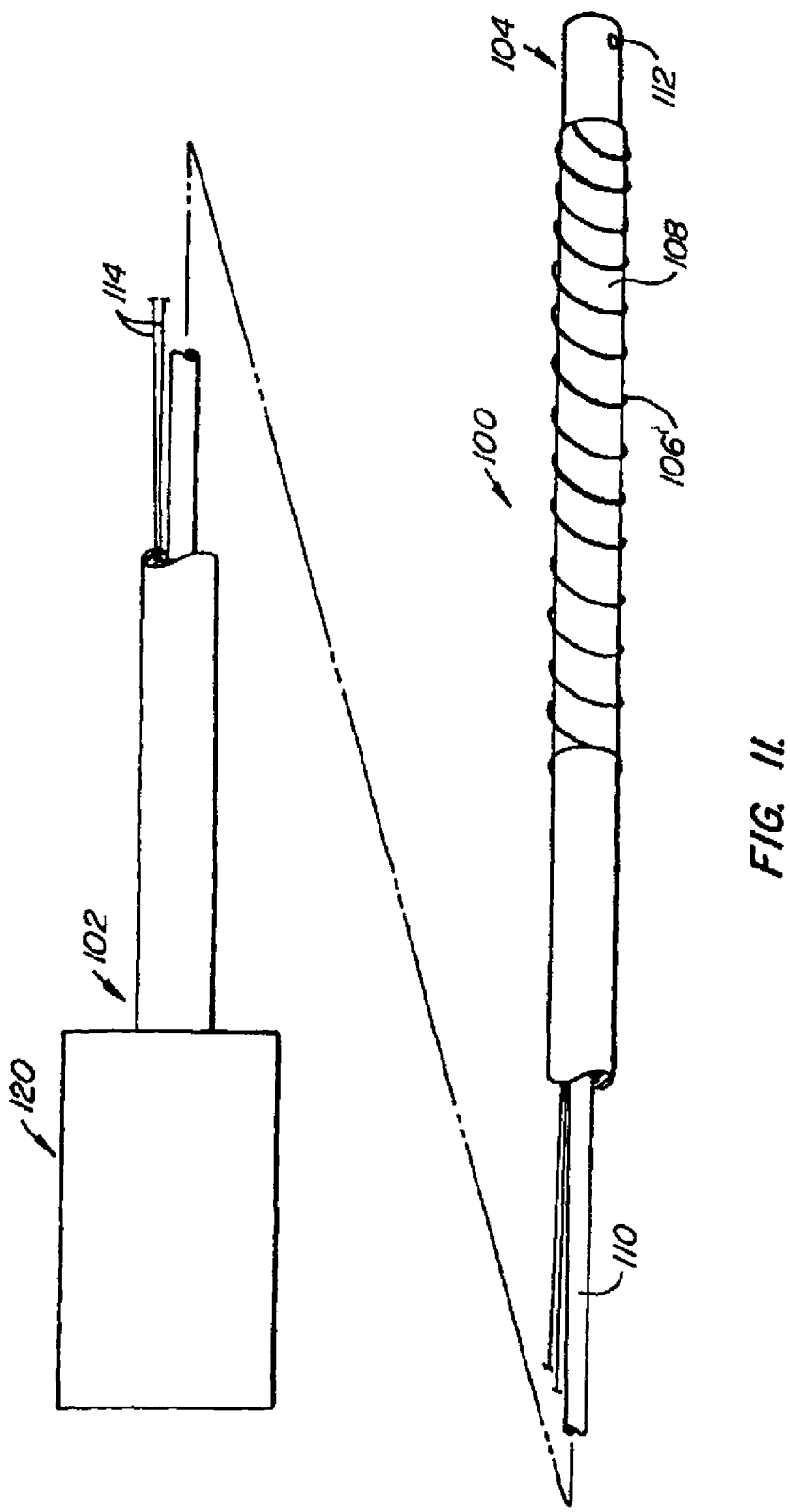
FIG. 11 illustrates a preferred catheter for the selective heating and cooling of patient blood How employing a wire coil resistance heater and a metal foil cooling element.

A preferred system for the selective warming and cooling of patients is illustrated in FIG. 11. The system comprises a catheter 100 having a proximal end 102, a distal end 104, a heat-generating surface 106 near the distal end, and a heat-absorbing surface near the distal end 108. The heat-generating surface 106 can be any of the heat transfer components described above, but will preferably be a wire coil resistance heater having from 50 to 1000 windings, typically spaced-apart from 0.1 mm to 1 mm. The total length of the catheter will typically be from 15 cm to 50 cm, and the diameter will be from 1 mm to 5 mm. Usually, the windings will extend over a total distance in the range from 10 cm to 20 cm near the distal end.

The exemplary heat-absorbing surface will be a thermally conductive metal foil, typically composed of a biologically compatible thermally conductive metal, such as gold, silver, aluminum, or the like. Copper will also be useful, but will have to be treated or encapsulated in order to enhance biocompatibility. The foil will typically be thin in order to enhance flexibility of the catheter body, typically having a thickness in the range from 0.001 mm to 0.01 mm.

The heat-absorbing surface 108 will be conductively coupled to a cooler located externally of the catheter, typically in a control unit 120 as described below, in the illustrated embodiment, the surface 108 is coupled by a thermally conductive core member 110 composed of a flexible rod or wire formed from one of the thermally conductive metals described above. Alternatively, thermal coupling can be achieved by extending the surface 108 proximally so that the proximal end of the surface can be coupled to the cooler. In the latter case, it will be preferable that the proximal portions of the surface 108 be thermally insulated to prevent cooling outside of the blood circulation.

The system will further comprise a control unit 120 which typically provides both the heat-generator and the cooler for coupling to the catheter 100. The heat-generator will usually comprise a direct current source for coupling to the resistance heater on the catheter. Usually, the direct current source will be a commercially available, temperature-controlled DC power supply, typically operating at a voltage in the range from 10 VDC to 60 VDC and a current output in the range from 1 A to 2.5 A. Usually, the power supply will be controlled to maintain the surface temperature of the heating surface 106 in the range from 40 degrees C. to 42 degrees C. As discussed above, the surface temperature should not exceed 42 degrees C. in order to prevent damage to blood components. Other desirable characteristics of the heat exchange surface are described above.

Optionally, the temperature of the heat exchange surface can also be controlled based on measured blood temperature and/or measured body temperature. Blood temperature can be measured by temperature sensors present on the catheter. For example, a temperature sensor 112 may be located on the catheter spaced-apart from the heat exchange surfaces 106 and 108. The temperature sensor 112 may be located either upstream or downstream from the heat exchange surfaces based on the direction of blood How and depending on the manner in which the catheter is introduced to the patient. Optionally, a pair of temperature sensors could be provided, one disposed on each side of the heat exchange surfaces in order to measure both upstream and downstream blood temperatures. The catheter will also include a temperature sensor (not illustrated) coupled directly to the heat-generating surface 106 so that the temperature of the surface may be directly controlled. Other temperature sensors (not illustrated) may be provided for directly measuring the patient's core body temperature, with the core body temperatures being fed back into the control unit 120.

The cooler in control unit 120 may be any type of refrigeration unit capable of removing heat from the heat-absorbing surface 106 at a rate sufficient to cool the blood at a desired rate. Typically, the cooler will be rated at from 1 W to 100 W. Preferably, the cooler will be a thermoelectric cooler, such as those commercially available from Melcor Thermoelectrics, Trenton, N.J. 08648. The cooler will be directly coupled to the core element 110 so that direct heat conduction from the heat-absorbing surface 108 may be effected to the cooler in control unit 120. The temperature of the cooling surface 108 is less critical than that of the heating surface 106, but will usually be maintained in the range from 0 degrees C. to 35 degrees C. preferably being below 30 degrees C. The temperature of the cooling surface may be directly controlled within this range, or alternatively the system may be designed so that the cooling temperature operates approximately within this range based on the total system characteristics.

The control unit 120 will further include one or more temperature controllers for controlling the temperature of the heat-generating surface 106 and the heat-absorbing surface 106 based on the blood temperature and/or the body temperature. At a minimum, the control unit 120 will provide for control of the temperature of the heat-generating surface 106 within the range set forth above, as well as for monitoring at least one of the patient blood temperature and patient body temperature in order to reverse the heating or cooling mode as discussed above. In the exemplary embodiment, as described in FIG. 10, the control scheme operates in an on-off mode, where for example hypothermic patients are initially treated by warming the blood at a constant surface temperature rate until a target temperature is reached. When the target temperature is reached, power to the heat-generating surface 106 is turned off. Monitoring of the blood and/or patient body temperature, however, is maintained to assure that the patient temperature does not exceed a maximum which is above the target temperature. Should the maximum be exceeded, then the system is operated in the cooling mode until the excess body temperature is lowered. Usually, there will be no need to again warm the patient, but the present system will provide for further cycles of warming and cooling if necessary. For initially hyperthermic patients, the cooling and warming modes are reversed.

It will be appreciated, for example, that the temperature control schemes of the present invention could be substantially more sophisticated. For example, the power input to warm the patient could be controlled based on proportional, derivative, or integral control schemes which will typically provide for a tapering of the heat transfer rate as the patient body temperature approaches the desired target level. Moreover, cascade control schemes based on both patient blood temperature and patient body temperature could be devised. Such control schemes, for example, could be adapted both for warming the patient and cooling the patient, with mathematical models of typical patient physiological characteristics being taken into account in preparing the control schemes. For the present, however, it is believed that a simple off-on control scheme with provision for reversing the heat transfer mode if the target temperature is exceeded by more than a safe amount will be sufficient.

What is claimed is:

1. A heat exchange catheter system comprising:
   an elongate, flexible catheter body a distal portion of which is insertable into the vasculature of a patient;
   a heat transfer surface disposed on less than the entirety of the distal insertable portion of the catheter body, said heat transfer surface comprising metal and having different thermal conductivity than the remainder of the distal insertable portion of the catheter body; and
   apparatus for alternately warming or cooling the heat transfer surface;

wherein the catheter body has a proximal end, a distal end, a heat exchange inflow lumen through which heat exchange fluid is deliverable from the proximal end of the catheter body to the area of the catheter body where the heat exchange surface is located and a heat exchange return lumen through which said heat exchange fluid may flow from the area of the catheter body where the heat exchange surface is located and back out of the proximal end of the catheter body.

2. A system according to claim 1 further comprising a temperature sensor.

3. A system according to claim 2 wherein the temperature sensor is useable to measure the temperature of a subject's blood when the catheter is inserted into that subject's vasculature.

4. A system according to claim 2 wherein the temperature sensor is located on or in the catheter body.

5. A system according to claim 4 wherein the temperature sensor is spaced-apart from the heat transfer surface.

6. A system according to claim 4 wherein the temperature sensor is located upstream of the heat exchange surface when the catheter is inserted into the subject's vasculature.

7. A system according to claim 4 wherein the temperature sensor is located downstream of the heat exchange surface when the catheter is inserted into the subject's vasculature.

8. A system according to claim 1 wherein the heat transfer surface comprises a metal selected from the group consisting of: gold, silver, aluminum and copper.

9. A system according to claim 1 wherein the heat transfer surface is located on a balloon through which the heat exchange fluid circulates.

10. A system according to claim 1 further comprising a control unit which controls the temperature of the heat transfer surface based on at least one measured temperature selected from the group consisting of: i) blood temperature and ii) body temperature.

11. A system according to claim 10 wherein the catheter body has at least two lumens defined in fluid communication with one another to allow for the circulation of fluid through the catheter and wherein the control unit operates to circulate heated or cooled heat exchange fluid through those lumens.

12. A system according to claim 11 wherein the control unit comprises extracorporeal heat transfer apparatus for heating or cooling the heat exchange fluid.

13. A system according to claim 11 wherein the heat transfer surface comprises a balloon that is inflatable by circulation of fluid through the lumens of the catheter body.

14. A system according to claim 1 wherein the apparatus for alternately warming or cooling the heat transfer surface includes a power supply capable of supplying peak power in the range between 100 and 1500 watts.

15. A system according to claim 14 wherein the power supply is capable of supplying peak power in the range between 300 and 1000 watts.

16. A system according to claim 1 wherein the catheter body further comprises means for increasing the effective heat transfer surface area.

17. A system according to claim 16 wherein the means for increasing the effective heat transfer surface area comprises a rib or fin.

18. A system according to claim 17 wherein the means for increasing the effective heat transfer surface area comprises a helical rib or fin.

19. A system according to claim 1 wherein the temperature of the heat transfer surface is controlled to deter overshooting s target body temperature.

20. A heat exchange catheter system comprising:
an elongate, flexible catheter body a distal portion of which is insertable into the vasculature of a patient;
a heat transfer surface disposed on less than the entirety of the distal insertable portion of the catheter body, said heat transfer surface comprising metal and having different thermal conductivity than the remainder of the distal insertable portion of the catheter body;
apparatus for alternately warming or cooling the heat transfer surface; and
a control unit which controls the temperature of the heat transfer surface based on at least one measured temperature selected from the group consisting of: i) blood temperature and ii) body temperature;
wherein the catheter body has at least two lumens defined in fluid communication with one another to allow for the circulation of fluid through the catheter and wherein the control unit operates to circulate heated or cooled heat exchange fluid through those lumens.

21. A system according to claim 20 further comprising a temperature sensor.

22. A system according to claim 21 wherein the temperature sensor is useable to measure the temperature of a subject's blood when the catheter is inserted into that subject's vasculature.

23. A system according to claim 21 wherein the temperature sensor is located on or in the catheter body.

24. A system according to claim 23 wherein the temperature sensor is spaced-apart from the heat transfer surface.

25. A system according to claim 23 wherein the temperature sensor is located upstream of the heat exchange surface when the catheter is inserted into the subject's vasculature.

26. A system according to claim 20 wherein the heat transfer surface comprises a metal selected from the group consisting of: gold, silver, aluminum and copper.

27. A system according to claim 20 wherein the catheter body has a proximal end, a distal end, a wherein the lumens comprise a heat exchange inflow lumen through which heat exchange fluid is deliverable from the proximal end of the catheter body to the area of the catheter body where the heat transfer surface is located and a heat exchange return lumen through which said heat exchange fluid may flow from the area of the catheter body where the heat exchange surface is located and back out of the proximal end of the catheter body.

28. A system according to claim 20 wherein the heat transfer surface is located on a balloon through which the heat exchange fluid circulates.

29. A system according to claim 23 wherein the temperature sensor is located downstream of the heat exchange surface when the catheter is inserted into the subject's vasculature.

30. A system according to claim 20 wherein the control unit comprises extracorporeal heat transfer apparatus for heating or cooling the heat exchange fluid.

31. A system according to claim 20 wherein the heat transfer surface comprises a balloon that is inflatable by circulation of fluid through the lumens of the catheter body.

32. A system according to claim 20 wherein the catheter body further comprises means for increasing the effective heat transfer surface area.

33. A system according to claim 32 wherein the means for increasing the effective heat transfer surface area comprises a rib or fin.

34. A system according to claim 33 wherein the means for increasing the effective heat transfer surface area comprises a helical rib or fin.

35. A system according to claim 20 wherein the temperature of the heat transfer surface is controlled to deter overshooting of the target body temperature.

* * * * *